(12) United States Patent
Schindelholz et al.

(10) Patent No.: US 10,969,359 B1
(45) Date of Patent: Apr. 6, 2021

(54) PLANAR ELECTRODE ARRAYS AND FABRICATION METHODS THEREOF

(71) Applicant: National Technology & Engineering Solutions of Sandia, LLC, Albuquerque, NM (US)

(72) Inventors: Eric John Schindelholz, Albuquerque, NM (US); Patrick Sean Finnegan, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 210 days.

(21) Appl. No.: 16/268,806

(22) Filed: Feb. 6, 2019

Related U.S. Application Data (60) Provisional application No. 62/631,581, filed on Feb. 16, 2018.

(51) Int. Cl.
| | | |
|---|---|---|
| *G01N 27/327* | (2006.01) | |
| *B81C 1/00* | (2006.01) | |
| *G01N 17/04* | (2006.01) | |
| *G01N 27/416* | (2006.01) | |
| *H05K 3/00* | (2006.01) | |

(52) U.S. Cl.
CPC ..... *G01N 27/3275* (2013.01); *B81C 1/00095* (2013.01); *G01N 17/04* (2013.01); *G01N 27/4163* (2013.01); *H05K 3/00* (2013.01); *B81C 2201/0125* (2013.01); *B81C 2201/0194* (2013.01); *H01L 2221/68304* (2013.01); *H01L 2221/68359* (2013.01)

(58) Field of Classification Search
CPC ............ G01N 27/3275; G01N 17/04; G01N 27/4163; H05K 3/00; B81C 1/00095; B81C 2201/0194; B81C 2201/0125; H01L 2221/68304; H01L 2221/68359
See application file for complete search history.

(56) References Cited

U.S. PATENT DOCUMENTS

| | | | |
|---|---|---|---|
| 5,324,687 A * | 6/1994 | Wojnarowski | H01L 21/6835 156/154 |
| 8,623,185 B2 | 1/2014 | Tormoen et al. | |
| 8,833,146 B2 | 9/2014 | Yu et al. | |
| 9,513,554 B1 | 12/2016 | Burckel et al. | |
| 9,659,797 B1 | 5/2017 | Burckel et al. | |
| 10,002,983 B1 | 6/2018 | Spoerke et al. | |
| 10,150,873 B2 | 12/2018 | Schindelholz et al. | |
| 2006/0151859 A1* | 7/2006 | Karkkainen | G02B 6/305 257/671 |
| 2015/0228416 A1* | 8/2015 | Hurwitz | H01G 4/1209 361/763 |

(Continued)

OTHER PUBLICATIONS

U.S. Appl. No. 15/336,099, filed Oct. 27, 2016, Burckel et al.

(Continued)

*Primary Examiner* — Yasser A Abdelaziez
(74) *Attorney, Agent, or Firm* — Helen S. Baca (57) ABSTRACT

The present invention relates to a method of fabricating an electrode array, in which an underlying handle wafer is removed to provide a planar device having the electrode array. Also provided are wafers including a plurality of planar devices having an electrode array, as well as sensors including such an electrode array.

14 Claims, 7 Drawing Sheets

(56) References Cited

U.S. PATENT DOCUMENTS

2018/0053745 A1* 2/2018 Cheng .................... H01L 24/20

OTHER PUBLICATIONS

U.S. Appl. No. 15/603,782, filed May 24, 2017, Schindelholz et al.
U.S. Appl. No. 15/624,928, filed Jun. 16, 2017, Finnegan et al.
U.S. Appl. No. 15/719,219, filed Sep. 28, 2017, Langlois et al.
Multi Channel Systems MCS GmbH, "Multielectrode Array (MEA) Manual," Jul. 2017 (68 pp.).

\* cited by examiner

PLANAR ELECTRODE ARRAYS AND FABRICATION METHODS THEREOF

CROSS-REFERENCE TO RELATED APPLICATION

This application claims the benefit of U.S. Provisional Application No. 62/631,581, filed Feb. 16, 2018, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates, in part, to a method of fabricating an electrode array, in which an underlying handle wafer is removed to provide a planar device having the electrode array. Also provided are wafers including a plurality of planar devices having an electrode array, as well as sensors including such an electrode array.

BACKGROUND OF THE INVENTION

High density, multielectrode arrays can be employed for electrical and electrochemical sensing. Fabrication of such arrays remains a challenge, in which current state of the art provides a limit of about 100 electrodes per $mm^2$. Yet, increasing the density of electrodes can provide improved signal resolution and enhanced spatial resolving power. Thus, additional manufacturing methodologies are needed for such improved multielectrode arrays.

SUMMARY OF THE INVENTION

The present invention relates, in part, to electrode arrays (e.g., planar, monolithic multielectrode arrays) and methods of fabricating such arrays. In particular embodiments, the array includes a plurality of electrodes, in which each electrode is individually addressable (e.g., each electrode is connected by a connector to a single bond pad). In this manner, individually addressable electrodes can be useful for electrochemical or electrical sensing applications.

Also provided herein are methods for fabrication such electrode arrays by employing a wafer transferring step. In some embodiments, the methods herein enables the creation of multielectrode arrays with higher density than current state of the art. The wafer transferring step include, in part, a fabrication process in which a device is initially provided upside down on a stack including a handle wafer (e.g., a carrier), then the stack is flipped, and then another wafer (i.e., a device wafer) is bonded to a top surface of the stack. Finally, the handle wafer is completely etched away, revealing the electrode array disposed (directly or indirectly) upon the device wafer.

The electrode arrays and methods thereof can employ any useful combination of material(s) (e.g., including layers thereof). In one non-limiting instance, the electrode array includes a planar array of electrodes with connectors (e.g., electrical leads) buried within a dielectric material, thereby allowing for electrical characterization of each electrode in isolation from other electrodes within the array.

In a first aspect, the present invention features a method of fabricating an electrode array. In some embodiments, the method includes: (i) providing a plurality of electrodes and a plurality of bond pads disposed on a top surface of a handle wafer; (ii) depositing a first metal to form a connector (e.g., where the connector is configured to form an electrical connection between at least one of the plurality of electrodes and at least one of the plurality of bond pads); (iii) depositing a bonding layer on at least a portion of a top surface of the dielectric layer; (iv) adhering a device wafer to a top surface of the bonding layer; and (v) removing the handle wafer, thereby forming a planar device.

In some embodiments, the planar device includes the device wafer, the bonding layer disposed on a surface of the device wafer, and an electrode array disposed within the dielectric layer. In other embodiments, the electrode array includes the at least one of the plurality of electrodes, the at least one of the plurality of bond pads, and the connector configured to form the electrical connection between the at least one of the plurality of electrodes and the at least one of the plurality of bond pads. In some embodiments, the handle wafer further includes a dielectric layer configured to isolate the plurality of electrodes and the plurality of bond pads.

In some embodiments, a depositing step (e.g., of a first metal, such as step (ii) in some methods herein) includes forming the electrical connection between one electrode and one bond pad. In other embodiments, a depositing step (e.g., of a first metal, such as step (ii) in some methods herein) includes forming a plurality of electrical connections, wherein each connection is between one electrode and one bond pad.

In some embodiments, the method further includes (e.g., after the depositing step, such as of a first metal, including step (ii) in some methods herein): planarizing the bonding layer. In other embodiments, the planarizing step thereby forms a planarized bonding layer to provide the top surface of the bonding layer (e.g., for an adhering step, such as to a device wafer, such as step (iv) in some methods herein).

In some embodiments, the method further includes: further including an initial bonding layer disposed between the plurality of electrodes and the top surface of the handle wafer. In other embodiments, the method further includes: further including a seed layer disposed between the initial bonding layer and the plurality of electrodes.

In some embodiments, the method further includes (e.g., after an adhering step, such as to a device wafer, such as step (iv) in some methods herein): removing the initial bonding layer. In some embodiments, the method further includes (e.g., after an adhering step, such as to a device wafer, such as step (iv) in some methods herein): removing the seed layer.

In some embodiments, the dielectric layer extends above a top surface of the plurality of electrodes (e.g., thereby providing a plurality of buried electrodes). In other embodiments, the dielectric layer extends of from about 100 nm to about 900 nm above the top surface of the plurality of buried electrodes. In yet other embodiments, the dielectric layer extends above a top surface of the plurality of bond pads (e.g., thereby providing a plurality of buried bond pads).

In a second aspect, the method features a method of fabricating an electrode array, the method including: (i) providing a plurality of electrodes, a plurality of bond pads, and a dielectric layer configured to isolate the plurality of electrodes and the plurality of bond pads; (ii) removing a portion of the dielectric layer (e.g., thereby forming a removed pattern connecting at least one of the plurality of electrodes to at least one of the plurality of bond pads); (iii)

depositing a first metal within the removed patterns (e.g., thereby forming an array of connectors, wherein each connector is configured to form an electrical connection between at least one of the plurality of electrodes and at least one of the plurality of bond pads); (iv) depositing a second bonding layer on at least a portion of a top surface of the dielectric layer; (v) planarizing the second bonding layer (e.g., thereby forming a planarized bonding layer); (vi) adhering a device wafer to a top surface of the planarized bonding layer; (vii) removing the handle wafer; and (viii) removing the first bonding layer and seed layer (e.g., thereby forming a planar device).

In some embodiments, the planar device includes the device wafer, the planarized bonding layer disposed on a surface of the device wafer, and an electrode array disposed within the dielectric layer. In other embodiments, the electrode array includes the plurality of electrodes, the plurality of bond pads, and the array of connectors configured to form electrical connections between at least one of the plurality of electrodes and at least one of the plurality of bond pads. In other embodiments, the plurality of electrodes and the plurality of bond pads are disposed on a top surface of a stack. In some embodiments, the stack includes a handle wafer having a top surface, a first bonding layer disposed on the top surface of the handle wafer, and a seed layer disposed on a top surface of the first bonding layer, in which the seed layer is disposed beneath a bottom surface of the plurality of electrodes and the plurality of bond pads.

In some embodiments, a depositing step (e.g., of a first metal, such as step (ii) in some methods herein) includes forming the electrical connection between one electrode and one bond pad. In other embodiments, a depositing step (e.g., of a first metal, such as step (ii) in some methods herein) includes forming a plurality of electrical connections, wherein each connection is between one electrode and one bond pad.

In a third aspect, the present invention includes a method of fabricating an electrode array, the method including: (i) providing a plurality of electrodes and a plurality of bond pads disposed on a top surface of a handle wafer (e.g., wherein the handle wafer further includes a dielectric layer configured to isolate the plurality of electrodes and the plurality of bond pads); (ii) depositing a first metal to form a plurality of connectors, wherein each of the plurality of connectors is configured to form an electrical connection between one of the plurality of electrodes and one of the plurality of bond pads; (iii) depositing a bonding layer on at least a portion of a top surface of the dielectric layer; (iv) adhering a device wafer to a top surface of the bonding layer; and (v) removing the handle wafer, thereby forming a planar device.

In some embodiments, the planar device includes the device wafer, the bonding layer disposed on a surface of the device wafer, and an electrode array disposed within the dielectric layer. In other embodiments, the electrode array includes the plurality of electrodes, the plurality of bond pads, and each of the plurality of connectors is configured to form an electrical connection between the one of the plurality of electrodes and the one of the plurality of bond pads.

In a fourth aspect, the present invention features a wafer including a plurality of planar devices (e.g., any described herein). In some embodiments, each planar device includes a device substrate, a bonding layer disposed on a surface of the device substrate, a dielectric layer disposed on a surface of the bonding layer, and an electrode array disposed within the dielectric layer. In other embodiments, the device substrate includes a portion of the wafer. In yet other embodiments, the electrode array includes a plurality of electrodes, a plurality of bond pads, and a plurality of connectors, wherein each of the plurality of connectors is configured to form an electrical connection between one of the plurality of electrodes and one of the plurality of bond pads. In some embodiments, the wafer includes of from about 20 to about 50 planar devices. In other embodiments, each electrode array includes of from about 20 to about 200 electrodes and of from about 20 to about 200 bond pads.

In a fifth aspect, the present invention features a sensor including: a planar device including a device substrate, a bonding layer disposed on a surface of the device substrate, a dielectric layer disposed on a surface of the bonding layer, and an electrode array disposed within the dielectric layer; a measurement circuit configured to be electrically connected to the electrode array (e.g., a plurality of connectors within the electrode array) and adapted to generate a signal indicative of a change in value of an electrical conductive property for at least one of the electrodes of the electrode array; and a digital computational device configured to receive the signal from the measurement circuit and in response thereto.

In some embodiments, the device substrate includes a portion of the wafer. In other embodiments, the electrode array includes a plurality of electrodes, a plurality of bond pads, and a plurality of connectors, wherein each of the plurality of connectors is configured to form an electrical connection between one of the plurality of electrodes and one of the plurality of bond pads.

In some embodiments, the sensor further includes: a digital memory embodying a data structure that relates values of the electrical conductive property to values of parameters that describe sensor history. In other embodiments, the digital computational device is configured to generate one of the signals of the sensor history further in response to values of said parameters retrieved from the digital memory.

In a sixth aspect, the present invention features a corrosion sensor including: a planar device including a device substrate, a bonding layer disposed on a surface of the device substrate, a dielectric layer disposed on a surface of the bonding layer, and an electrode array disposed within the dielectric layer; a measurement circuit configured to be electrically connected to the electrode array (e.g., to a plurality of connectors of the electrode array) and adapted to generate a signal indicative of a change in value of an electrical conductive property for at least one electrode of the electrode array (e.g., of the plurality of electrodes); and a digital computational device configured to receive the signal from the measurement circuit and in response thereto, to generate a signal indicative of corrosion of the electrode array.

In some embodiments, the device substrate includes a portion of the wafer. In other embodiments, the electrode array includes a plurality of electrodes, a plurality of bond pads, and a plurality of connectors, wherein each of the plurality of connectors is configured to form an electrical connection between one of the plurality of electrodes and one of the plurality of bond pads In some embodiments, the corrosion sensor further includes: a digital memory embodying a data structure that relates values of the electrical conductive property to values of parameters that describe corrosion history, wherein the digital computational device is configured to generate the corrosion-indicative signal further in response to values of said parameters retrieved from the digital memory.

In a seventh aspect, the present invention features a biological sensor including: a planar device including a device substrate, a bonding layer disposed on a surface of the device substrate, a dielectric layer disposed on a surface of the bonding layer, and an electrode array disposed within the dielectric layer; a plurality of biological cells disposed in proximity to the electrode array; a measurement circuit configured to be electrically connected to the electrode array (e.g., to the plurality of connectors of the electrode array) and adapted to generate a signal indicative of a change in value of an electrical conductive property for at least one electrode of the electrode array (e.g., one of the plurality of electrodes); and a digital computational device configured to receive the signal from the measurement circuit and in response thereto, to generate a signal indicative of cellular activity of at least one of the plurality of biological cells in proximity to the electrode array.

In some embodiments, the device substrate includes a portion of the wafer. In other embodiments, the electrode array includes a plurality of electrodes, a plurality of bond pads, and a plurality of connectors, wherein each of the plurality of connectors is configured to form an electrical connection between one of the plurality of electrodes and one of the plurality of bond pads. Additional details follow.

Definitions

As used herein, the term "about" means+/−10% of any recited value. As used herein, this term modifies any recited value, range of values, or endpoints of one or more ranges.

By "micro" is meant having at least one dimension that is less than 1 mm and, optionally, equal to or larger than about 1 µm. For instance, a microstructure (e.g., any structure described herein) can have a length, width, height, cross-sectional dimension, circumference, radius (e.g., external or internal radius), or diameter that is less than about 1 mm. In another instance, the microstructure can have a dimension that is less than about 1 mm and equal to or larger than about 1 µm.

By "nano" is meant having at least one dimension that is less than 1 µm but equal to or larger than about 1 nm. For instance, a nanostructure (e.g., any structure described herein, such as a nanoparticle) can have a length, width, height, cross-sectional dimension, circumference, radius (e.g., external or internal radius), or diameter that is less than about 1 µm. In another instance, the nanostructure can have a dimension that is less than about 1 µm and equal to or larger than about 1 nm. In yet other instance, the nanostructure has a dimension that is of from about 1 nm to about 1 µm.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

DETAILED DESCRIPTION OF THE INVENTION

The present invention relates, in part, to a planar multielectrode array with individually addressable electrodes, as well as method of fabricating such arrays.

Figure 5:
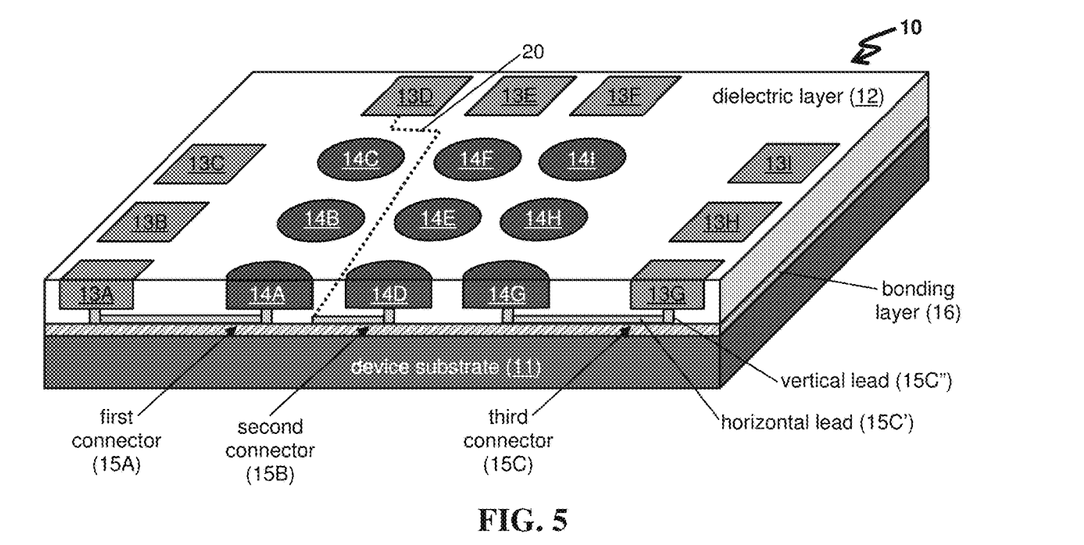
FIG. 5 shows a schematic of an exemplary device 10 including an electrode array.

FIG. 5 shows an exemplary electrode array 10 including a plurality of electrodes 14A-14G, a plurality of bond pads 13A-13G, and a plurality of connectors 15A-15C (e.g., buried connectors). The array is disposed upon a device substrate 11 and within a dielectric layer 12. Optionally, a bonding layer 16 is disposed between a top surface of the device substrate 11 and the bottom surface of the dielectric layer 12.

Optionally, the device can include each electrode connected to one bond pad, thereby providing individually addressable electrodes. As seen in FIG. 5, a first electrode 14A is electrically connected to a first bond pad 13A by way of a first connector 15A. As can be seen, each of the first, second, and third electrodes 14A,14D,14G is electrically connected to one of the first, second, and third bond pads 13A,13F,13G, respectively, by way of a first, second, and third connector, 15A,15B with 20,15C, respectively.

Figure 6:
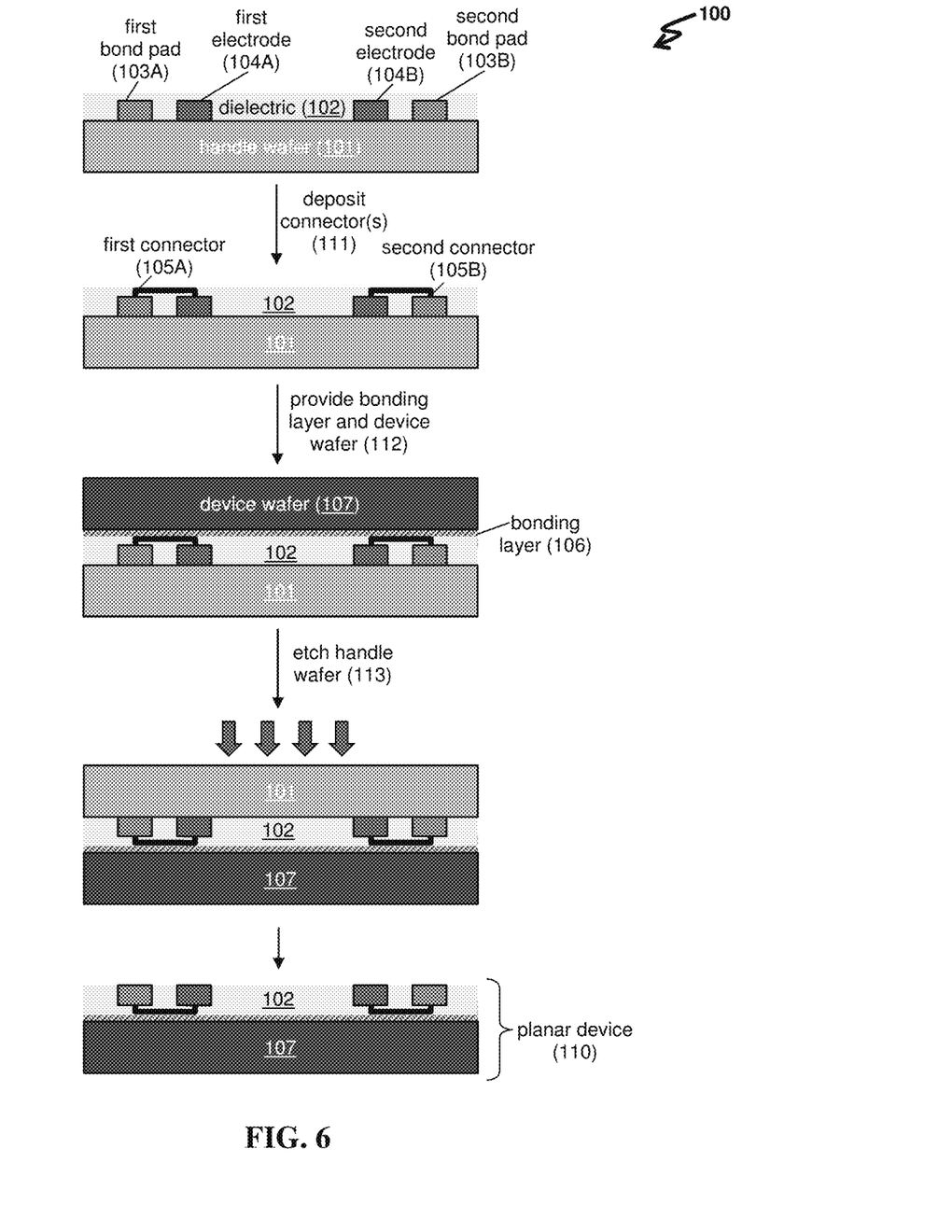
FIG. 6 shows a schematic of an exemplary method 100 for fabricating an electrode array.

The arrays can be fabricated in any useful manner. FIG. 6 provides an exemplary method 100 of fabricating an electrode array. As can be seen, the method includes providing a first stack, which includes a plurality of electrodes 104A,104B and a plurality of bond pads 103A,103B disposed on a top surface of a handle wafer 101. The first stack also includes a dielectric layer 102 configured to isolate the plurality of electrodes from the plurality of bond pads.

Next, a first metal is deposited 111 to form a connector 105A,105B (e.g., a buried connector). In particular, the connector is configured to form an electrical connection between at least one of the plurality of electrodes and at least one of the plurality of bond pads. In some embodiments, each connector is configured to form an electrical connection between one electrode and one bond pad.

Then, a device wafer 107 is provided 112 to the first stack, thereby providing a bonded stack including a handle wafer 101, a dielectric layer 102, an electrode array (e.g., including electrodes, bond pads, and connectors), and a device wafer 107. In some embodiments, a bonding layer 106 is provided between the device wafer 107 and the dielectric layer 102. In some embodiments, the bonding step includes depositing a bonding layer on at least a portion of a top surface of the first stack (e.g., the top surface of the dielectric layer); and adhering a device wafer to a top surface of the bonding layer.

Finally, the handle wafer is removed 113, e.g., by way of etching. In this way, a planar device 110 is formed. In some embodiments, the planar device includes a device wafer, a bonding layer disposed on a surface of the device wafer, and an electrode array disposed within the dielectric layer. In other embodiments, the electrode array includes at least one electrode, at least one bond pad, and a connector configured to form the electrical connection between the electrode and the bond pad.

Figure 7:
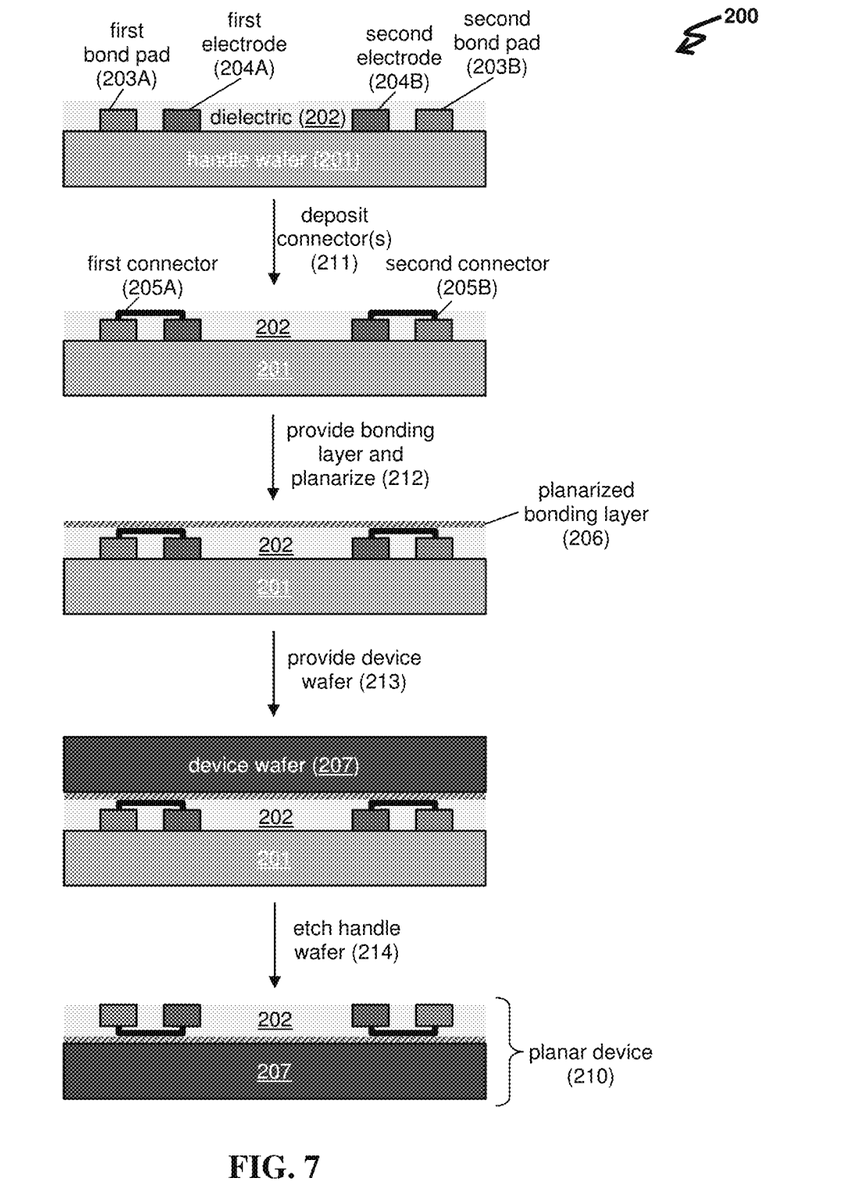
FIG. 7 shows a schematic of another exemplary method 200 for fabricating an electrode array.

The method can include any other useful step, such as planarizing any layer, depositing any layer, or depositing any useful material (e.g., a conductive material, by way of photolithograph). FIG. 7 shows an exemplary method 200 including a planarizing step 212. As can be seen, the method 200 can include providing a first stack, which includes a plurality of electrodes 204A,204B; a plurality of bond pads 203A,203B disposed on a top surface of a handle wafer 201; and a dielectric layer 202 configured to isolate the plurality of electrodes from the plurality of bond pads.

Next, a first metal is deposited 211 to form a connector 205A,205B (e.g., a buried connector). Then, a bonding layer is provided and planarized 212, thereby providing a planarized bonding layer 206 within the planarized stack. A device wafer 207 is provided 213 to the planarized stack, thereby providing a bonded stack including a handle wafer 201, a dielectric layer 202, an electrode array (e.g., including electrodes, bond pads, and connectors), a planarized bonding layer 206, and a device wafer 207. Finally, the handle wafer is removed 214, e.g., by way of etching. In this way, a planar device 210 is formed.

The method can include providing further layers within the stack, bonded stack, or planar device.

Figure 8:
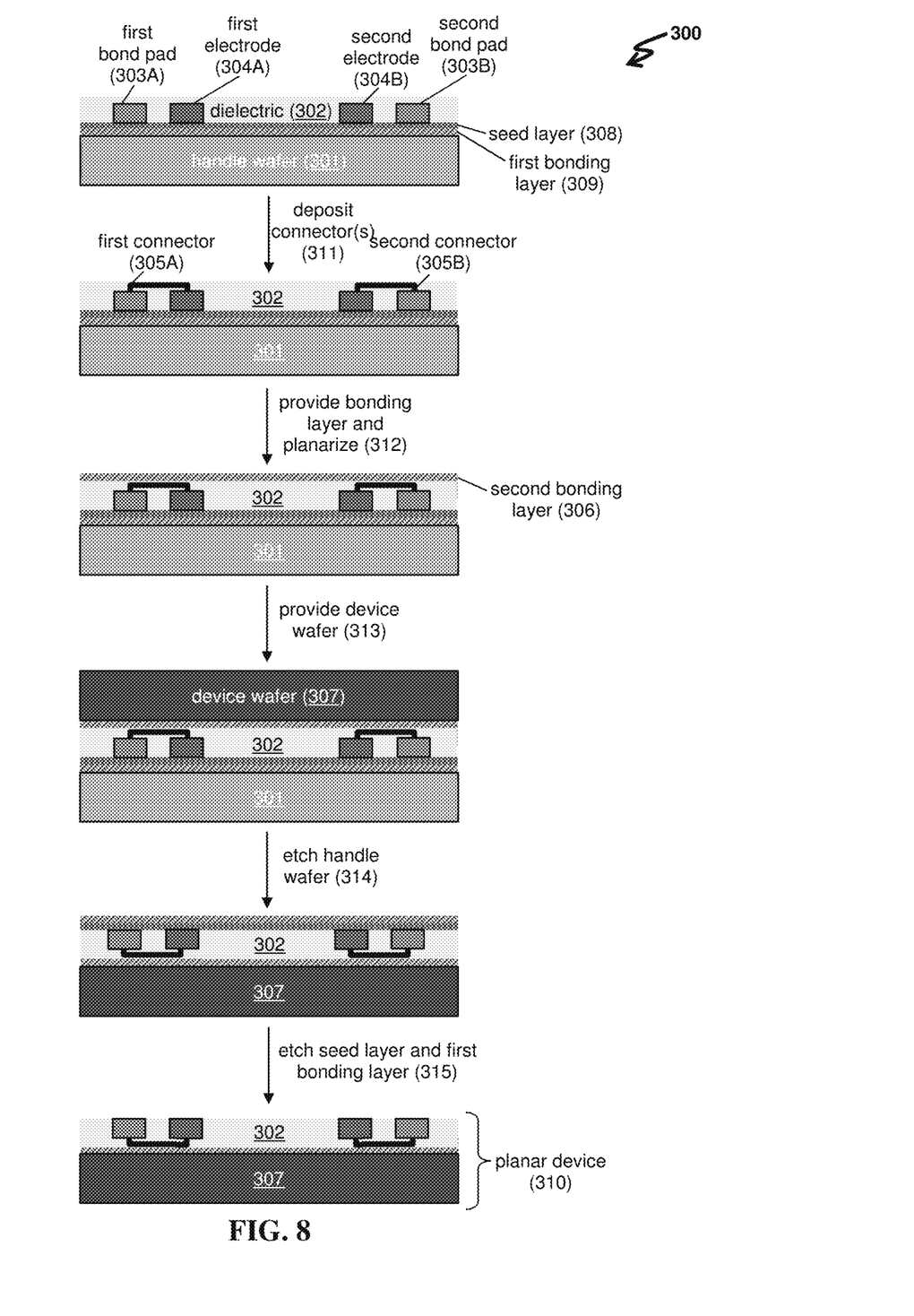
FIG. 8 shows a schematic of a yet another exemplary method 300 for fabricating an electrode array.

FIG. 8 shows an exemplary method 300 including a planarizing step 312 and a further etching step 315. As can be seen, the method 300 can include providing a first stack, which includes a plurality of electrodes 304A,304B; a plurality of bond pads 303A,303B disposed on a top surface of a handle wafer 301; a seed layer 308 disposed beneath a bottom surface of the electrodes; a first bonding layer 309 disposed between the seed layer 308 and the handle wafer 301; and a dielectric layer 302 configured to isolate the plurality of electrodes from the plurality of bond pads.

Next, a first metal is deposited 311 to form a connector 305A,305B (e.g., a buried connector). Then, a second bonding layer 306 is provided and planarized 312, thereby providing a planarized bonding layer within the planarized stack. A device wafer 307 is provided 313 to the planarized stack, thereby providing a bonded stack including a handle wafer 301, a first bonding layer 309, a seed layer 308, a dielectric layer 302, an electrode array (e.g., including electrodes, bond pads, and connectors), a second bonding layer 306 that is planarized, and a device wafer 307. The handle wafer is removed 314, e.g., by way of etching; and then the seed layer and first bonding layer are removed 315, e.g., by way of etching. In this way, a planar device 310 is formed.

The arrays herein can be employed in any useful manner. Multielectrode arrays can be used to spatially resolve electrical current or electric potential gradients that develop between the electrodes during electrochemical processes. Electrochemical reactions generally involve transfer of electrons from one species (i.e., atom, ion, molecule, etc.) to another, resulting in a change in oxidation state of both species. This change in oxidation state occurs by way of oxidation and reduction, in which these reactions are separated by an electric path that occurs in an intervening electrolyte and between an anode and a cathode. The transfer of electrons between anode and cathode sites creates electric current and potential gradients, and such changes in currents and gradients can be detected by way of an electrode array. By employing a spatial arrangement of electrodes, the electrical signal can be spatially resolved, in which the resolution is limited, in part, by the size of the array and the density of electrodes within the array.

Non-limiting applications for planar multielectrode arrays include use as electrochemical sensors, such as for environmental studies or studies of biological cells. One non-limiting application includes use as a corrosion sensor, in which oxidation of one or more metallic sensor electrodes and transfer of electrons to one or more other electrodes in the array, where cathodic processes are occurring, can be measured via measurements of electrical current or potential differences between electrodes. In biological systems, electrical activity of cells and tissues can be monitored by transduction of ionic currents due to cell activity to potentials measured across the array. In this manner, non-invasive recordings of extracellular electrical signals can be made measured in vitro or in vivo conditions. Other non-limiting applications that can benefit from spatially resolved electrochemical sensing including corrosion analysis, embedded corrosion health monitoring, electrophysiology determination, and electrocatalysis testing.

The electrode array can have any useful characteristic, such as a height of particular layers, number of electrodes, size of electrodes, spacing between electrodes, and location of bond pads. In one instance, electrode size and interelectrode spacing can be selected to a desired spatial resolving power of the electrode array. In general, spatial resolution increases with smaller electrodes and interelectrode spacing. Increased resolution can be advantageous, for example, in corrosion and biological sensing applications. In corrosion applications, micro to sub-microscale localized corrosion events, such as initiation of pits, can be resolved with electrode and interelectrode dimensions of the same or smaller size scale. Furthermore, as interelectrode spacing decreases, the array approaches a continuous metallic surface. In turn, this design can be employed to minimize the interfering effects of a dielectric between the surface, better emulating a freely corroding surface. The electrodes can have any useful size, including dimensions scalable from submicron (e.g., electron beam lithography) to macroscale (e.g., contact lithography).

The arrays and methods herein can be employed to overcome fabrication limitations. For instance, in one instance, the current state of the art provides a limitation for planar multielectrode array electrode density of about 100 electrodes/$mm^2$ by using microfabrication and embedded wire fabrication. In particular, for microfabricated arrays in which electrodes and connectors are on the same plane, density and maximum size of the array are limited by the necessity to route connectors.

In one embodiment, the present invention includes a system and method of providing a lithography-manufactured integrated circuit, in which the circuit includes a plurality of electrodes (e.g., any described herein). In some embodiments, each bond pad is entirely planar with a top surface of a dielectric layer. In other embodiments, each bond pad is inset within a dielectric surface (e.g., thereby providing a buried bond pad).

In some embodiments, the device is a high density planar, multilevel electrode array. In particular, the methods herein (e.g., planarization and bonding techniques combined with various etching steps) include removal of the handle wafer (carrier wafer), which in turn enables a high density planar, multilevel electrode array. In other embodiments, planarity is maintained by fabrication of devices on a handle wafer, which is subsequently inverted and bonded to a device wafer. The handle wafer is then etched away leaving an all planar device on the device wafer.

In other embodiments, the device includes buried connectors, in which passivated electrode traces are buried underneath the electrode array on separate level(s). In some embodiments, touting the connectors at levels below the electrodes eliminates requirement to route connectors between the electrodes, thus eliminating electrode spacing restrictions.

In some embodiments, a contiguous electrode surface can be emulated by minimizing electrode spacing. This feature is advantageous, e.g., for study of freely corroding surfaces, where dielectric spacing between the electrodes can influence corrosion behavior (current and potential distributions).

Exemplary Materials

Any useful material herein can be employed for the electrode arrays and methods thereof. Exemplary materials include a dielectric to isolate electrodes and/or bond pads, e.g., silicon dioxide (e.g., $SiO_2$), silicon nitride (e.g., $Si_3N_4$), SiN, silicon oxynitride (e.g., SiON or $SiO_xN_y$), or a polymer, as well as doped forms thereof. Any useful conductive material can be employed to form the electrodes and bond pads herein, in which the same or different materials can be employed for the electrodes and bond pads. Furthermore, conductive materials can be provided as a single material, a bulk material, a thin film, or a stack including a plurality of materials. Exemplary conductive materials include copper (Cu), silver (Ag), aluminum (Al), tungsten (W), titanium (Ti), platinum (Pt), gold (Au), germanium (Ge), iridium (Ir), tantalum (Ta), nickel (Ni), aluminum (Al), as well as alloys or combinations thereof (e.g., Al—Cu, Au—Cu, Cu—Sn, Au—Ti, or Au—Ni), and highly conductive ceramics such as titanium nitride. Such conductive materials can be deposited and then further treated, e.g., annealed.

Other useful layers can be employed, including a barrier layer (e.g., to minimize diffusion of atoms out of a particular region), a buffer layer, an epitaxial layer, a seed layer, a bonding layer, a metallization layer, an interlayer, an insulation layer, a sacrificial layer, etc. The various layers are deposited, e.g., on a substrate that may be highly doped to provide back-side electrical contact. Exemplary substrates include, e.g., a silicon substrate (such as a silicon wafer) that be optionally treated (e.g., oxidized) or coated (e.g., with a bonding layer, such as one including silicon dioxide or benzocyclobutene (BCB); or with a seed layer, such as one including one or more conductive materials, e.g., Au—Ti, TiN, Au—Sn, Au—Si, Au—Ge, Al—Ge, or Au—In).

Any useful process can be employed with the methods disclosed herein. Exemplary processes include epitaxial growth; wafer bonding (e.g., adhesive bonding, anodic bonding, direct bonding, eutectic bonding, plasma activated bonding, reactive bonding, surface activated bonding, and thermocompressive bonding); polishing, such as chemical-mechanical polishing (CMP); chemical vapor diffusion (CVD), such as metal-organic CVD (MOCVD), metal-organic vapor phase epitaxy (MOVPE), plasma-enhanced chemical vapor deposition (PECVD), and molecular beam epitaxy (MBE); milling (e.g., ion milling or focused ion beam milling); rapid prototyping; microfabrication (e.g., by casting, injection molding, compression molding, embossing, ablation, thin-film deposition, and/or Computer Numerically Controlled (CNC) micromachining); photolithography; atomic layer deposition (ALD); and etching techniques (e.g., wet chemical etching, reactive ion etching (RIE), deep RIE, sputter etching, inductively coupled plasma deep silicon etching, buffered oxide etching (BOE), laser ablation, or air abrasion techniques). In one instance, the electrodes and bond pads can be constructed of any conductive material deposited via physical or electrochemical deposition. Alternatively, semiconductor electrode features could be constructed via ion implantation.

EXAMPLE

Example 1: Planar, Monolithic High Density Multielectrode Array for Electrochemical Sensing and Method of Manufacture Herein, we provide an exemplary manufacturing process and design of high-density, planar multielectrode arrays with integrated electrical traces. Such arrays can be used, e.g., to measure electrical characteristics in situ, which in turn requires passivating the routing signal circuitry so that only the electrode array is exposed to environmental or testing conditions. In part, the exemplary process includes fabricating the device so that the design of the finalized device is fabricated upside down on a first wafer (i.e., a handle wafer). A second wafer (i.e., a device wafer) is then bonded to the handle wafer, which is completely etched away, thereby revealing the electrode array.

Electrical isolation of electrodes can be achieved by employing a dielectric layer, in which dielectric material is disposed between the electrodes and the bond pads. An electrical connection between an electrode and a bond pad is achieved by employing a connector. Thus, an exemplary finalized device can include a planar array of electrodes with connectors (e.g., electrical leads) buried within a dielectric material below, thereby allowing for electrical characterization of each electrode in isolation from the other electrodes within the array.

The methods herein can be employed with any useful material (e.g., conductive material, dielectric material, etc.). In certain instances, the wafer transfer manufacturing method described herein can be used to select different material sets (e.g., electrodes, traces, and dielectric) to provide optimal fabrication quality that also meets end-use requirements.

Figure 1:
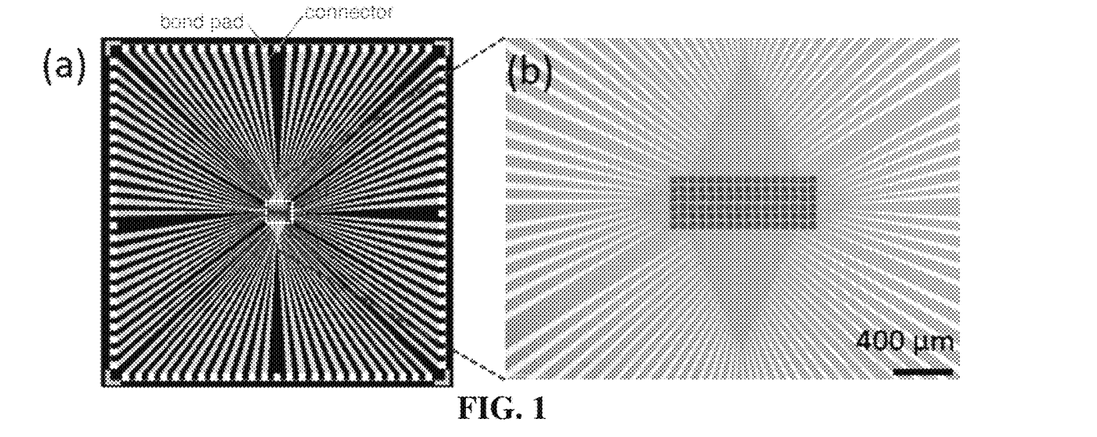
FIG. 1 shows an exemplary electrode array. Provided is (a) a drawing of a 96-electrode device with an electrode array (noted by dashed rectangle), bond pads (white rectangles), and connectors (or traces leading from each electrode to a bond pad); and (b) a micrograph of the underside of an 96-electrode array during manufacture, in which a copper electrode array and gold trace routing are visible.

FIG. 1 shows an exemplary device that is constructed of copper electrodes with gold bond pads and buried gold connectors (or traces). FIG. 1(a) provides detail of the 6×16 electrode array, demonstrating the ability to create larger (e.g., 96 electrodes) and higher density (e.g., 240 electrodes/$mm^2$) arrays of individually addressable electrodes than the current state of the art. Even higher density and larger arrays could be achieved by decreasing electrode size and inter-electrode spacing using the manufacturing method described herein.

Figure 2:
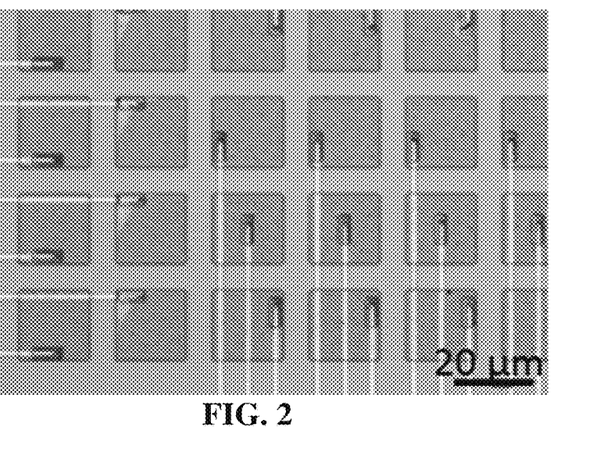
FIG. 2 shows a micrograph of the underside of an exemplary electrode array showing gold traces that connect to copper electrodes.
Figure 3:
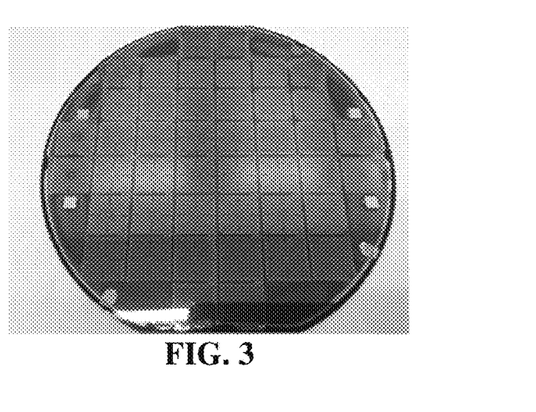
FIG. 3 shows a photograph of a complete fabricated 150 mm wafer with 42 devices, in which each device includes an electrode array.
Figure 4:
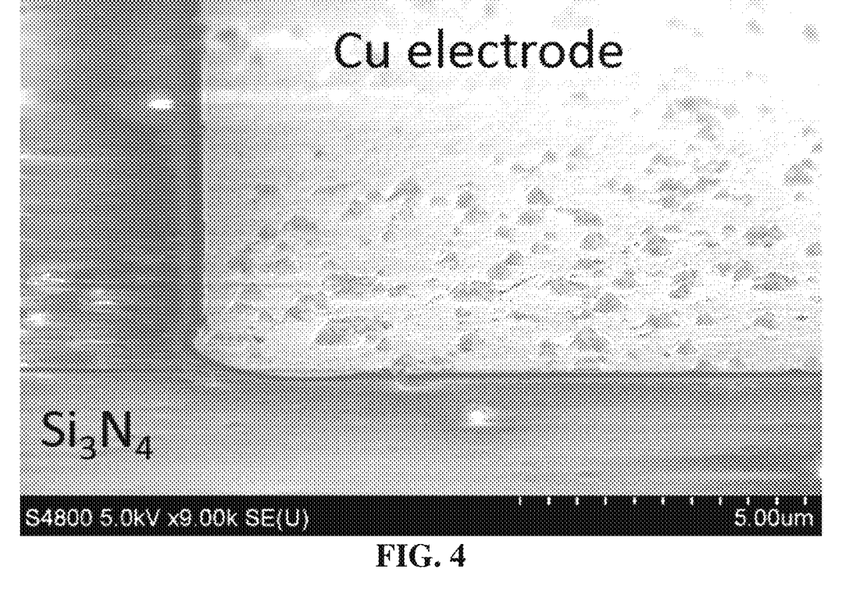
FIG. 4 shows a secondary electron image of the face of an electrode array device detailing the planarity of a copper electrode with respect to the dielectric (e.g., $Si_3N_4$) surface.

FIG. 2 is an image taken during construction, which shows the electrode trace routing (insulated from the copper electrodes) on the backside that enables the large and high density array design. A completed wafer with the devices is shown in FIG. 3. The image in FIG. 4 demonstrates the planarity achieved using the exemplary manufacturing technique described here. Additional chemo-mechanical or electrochemical polishing steps could be utilized to further reduce roughness of the copper electrode surface.

FIG. 9A-9F illustrates one exemplary process to produce the device shown in FIG. 1(a) and FIG. 2, which shows an array of copper electrodes in a dielectric (e.g., a $Si_3N_4$ matrix) and corresponding gold bond pads connected by gold traces. Each of these steps is described below.

Figure 9A:
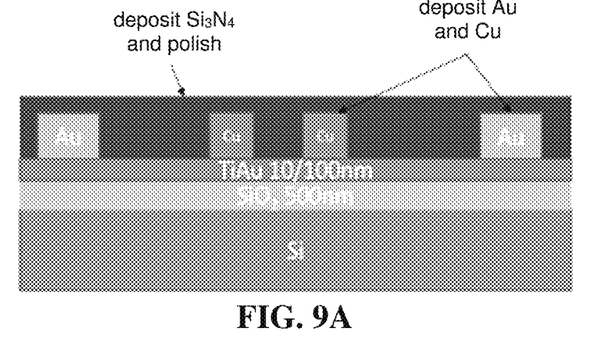
FIG. 9A-9F shows an exemplary fabrication method to create high density, planar multielectrode array devices, in which steps are illustrated showing cross-sectional views of the exemplary device.

As seen in FIG. 9A, initial steps include construction of copper electrodes and gold bond pads on a handle wafer. First, a silicon dioxide ($SiO_2$) layer is grown on the silicon handle wafer, e.g., using a plasma-enhanced chemical vapor deposition (PECVD) process. A metal layer of titanium and gold (TiAu) is then deposited on the $SiO_2$ layer. This TiAu layer serves as a seed metal for the electrochemical deposited Cu electrodes, as well as the Au contact/bond pads of the device. Then, a dielectric material (e.g., a dielectric layer, such as a 1 μm thick $Si_3N_4$ film) is then deposited on top of the seed metal layer.

Into this dielectric material, an array of electrodes and bond pads is defined. In one non-limiting instance, the electrode array is photolithographically patterned onto the surface of dielectric, and this pattern is transferred into the dielectric layer by etching down to the seed layer, e.g., by using a reactive ion etch (RIE) process. A desired metal (e.g., here, Cu) is electroplated up to the surface of the dielectric to form the plurality of Cu electrodes. A bond pad pattern is then aligned, photolithographically defined to the existing Cu electrode array, and etched using RIE down to the seed layer. A desired second metal (e.g., here Au) is electroplated to form the contact pads. Each Au bond pad can correspond to one of the Cu electrodes in the array. In one instance, the height of the electrodes and bond pads is about 1 μm thick.

The array of electrodes and bond pads can then be passivated. In one embodiment, a dielectric material (e.g., $Si_3N_4$) is deposited (e.g., by way of CVD) on top of the Cu and Au plated electrodes and bond pads. In this way, the electrode array can be passivated so that metal traces can be used to bridge across each electrode without shorting the electrodes to one another. The dielectric layer can be extended above the electrodes, thereby providing buried electrodes with an extended dielectric material located above a top surface of the electrode. In one non-limiting instance, the extended material provides about 100 nm to about 900 nm of dielectric material located above a top surface of the electrode. For example, if the electrode is about 1 μm high, then the dielectric layer is of from about 1.1 μm to about 2 μm high (as determined from a top surface of the seed layer, which in turn is disposed on a top surface of the silicon oxide bonding layer and/or handle wafer). The dielectric layer can be planarized, e.g., by way of chemo-mechanical polishing (CMP).

Figure 9B:
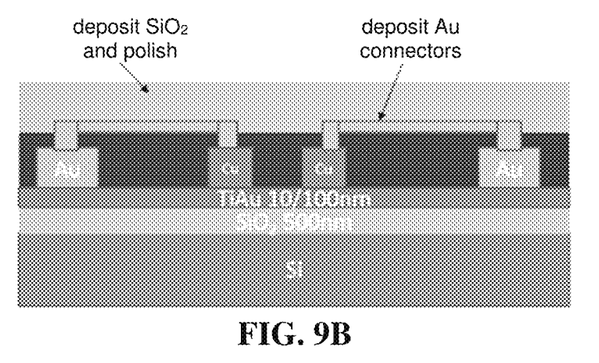

FIG. 9B illustrates construction of Au connectors connecting the Au bond pads to the Cu electrodes, followed by construction of a bonding layer (e.g., an $SiO_2$ layer) that will serve to bond the resulting stack to a device wafer. In order to selectively make contact to each of the Cu electrodes, the dielectric layer (here, the $Si_3N_4$ layer) is patterned and opened by photolithography, thereby defining a pattern that allows for vertical leads (e.g., Au leads) to make contact with a single electrode and be routed to a single bond pad, without making contact any other electrode or bond pad. Next, another photolithography step defines the horizontal leads that connects a vertical lead from each of the electrodes to a bond pad. The vertical and horizontal leads, together, form a contiguous connector between an electrode and a bond pad.

Metal deposition of the connector can employ any useful process, such as a standard liftoff process. In an exemplary liftoff process, a photoresist pattern is provided on a surface, in which the areas lacking photoresist result in adhered metal and areas having photoresist can be masked. By employing a solvent to dissolve the resist, a metal deposited on top of the resist is lifted off, thereby leaving the desired pattern.

Electrical isolation of the connector can be achieved by depositing a bonding layer, in which the material is a dielectric that also facilitates bonding of a wafer to the stack. To maintain electrical isolation, an extended bonding material can be located above a top surface of the electrode. In one non-limiting instance, the extended material provides about 100 nm to about 900 nm of bonding material located above a top surface of the buried connector. For example, if the connector is about 200 nm high, then the bonding layer is of from about 500 nm to about 1 μm high (as determined from a top surface of the dielectric layer). The bonding layer can be planarized, e.g., by way of chemo-mechanical polishing (CMP). In one instance, as seen in FIG. 9B, a thick $SiO_2$ film is deposited on top of the entire wafer and then chemo-mechanically polished to achieve a planar surface. The planarity of the $SiO_2$ in this step allows for the device wafer to be bonded to this surface, as shown in the next step.

Figure 9C:
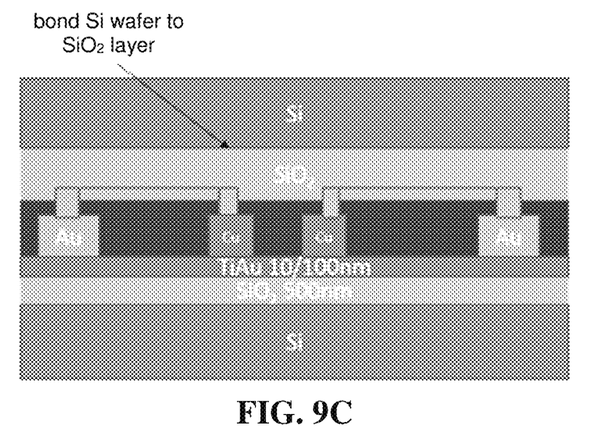

FIG. 9C shows bonding of a device wafer to the resulting stack. A new wafer (e.g., a Si wafer) that will become the device wafer is introduced to the process. In one non-limiting instance, the device wafer has an optional interlayer (e.g., a $Si_3N_4$ layer grown on the top and bottom surfaces, e.g., by way of a diffusion furnace), in which the interlayer allows the wafer to be subjected to different chemistries without etching the underlying substrate. In yet another non-limiting instance, the device wafer includes a bonding layer (e.g., an $SiO_2$ layer deposited by way of CVD, which can be deposited directly on a surface of the wafer or deposited on top of the interlayer disposed on the wafer). Optionally, the device wafer can be further treated (e.g., touch polished by way a CMP) to achieve a smooth surface to be mated to the $SiO_2$ layer on the stack (e.g., the stack as shown in FIG. 9B). The new device wafer and the stack can then be cleaned and then bonded to one another (e.g., using heat and/or pressure or by using a surface reaction) to create a bonded stack (e.g., by way of a covalent bond).

Figure 9D:
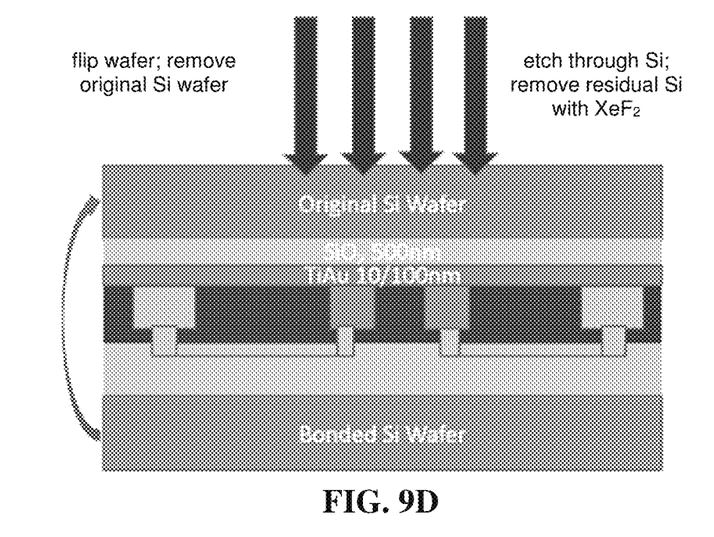

Next, the handle wafer is removed from the bonded stack. The handle wafer and underlying layers (e.g., the seed layer and/or bond layer) can be removed in any useful manner. As seen in FIG. 9D, the handle wafer is removed by way of a Bosch etch and/or a $XeF_2$ etch. Using a Bosch etch, silicon can be etched in a deep reactive ion etch using $XeF_2$ chemistry. Another method includes physically grinding the bulk of the silicon material (e.g., by way of a back grinder) and then removing residual silicon by way of a chemical etch (e.g., a spray acid tool administering a nitric and hydrofluoric acid chemistry).

Figure 9E:
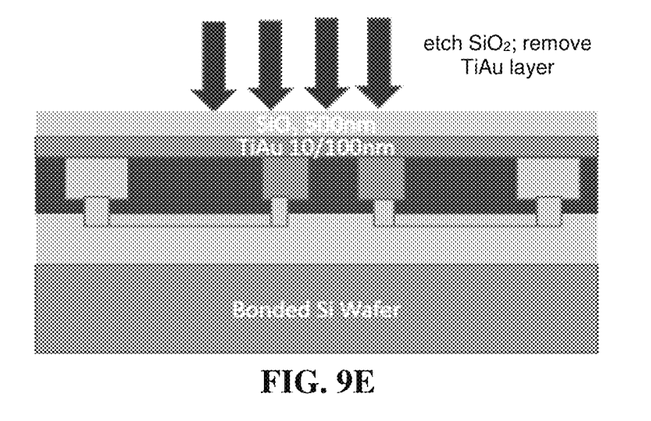
Figure 9F:
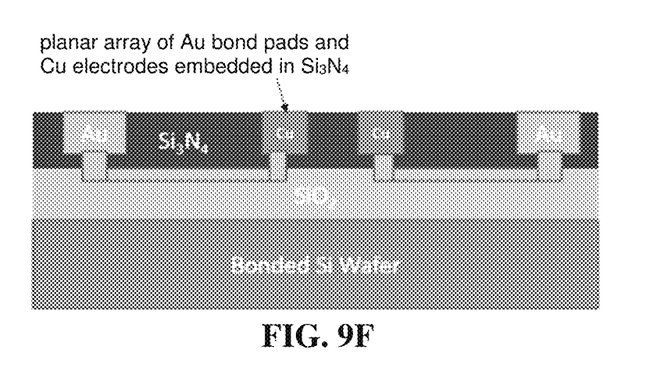

Then, the underlying bonding layer in proximity to the handle layer (e.g., the $SiO_2$ layer) and the underlying seed layer (e.g., the TiAu layer) can be removed in any useful way, as seen in FIG. 9E. The bonding layer can be etched, e.g., by way of BOE or RIE and Ar; and the seed layer can also be removed in any useful manner, e.g., by way of an ion mill, which physically sputters the metal off of the wafer, thereby revealing the planar electrode array and bond pads (FIG. 9F). The wafer can then be diced to separate each die, each of which can then be wire bonded into a package to facilitate testing.

The planar device can have any useful characteristic. In one embodiment, the device includes a plurality of electrodes (e.g., having a height of from about 200 nm to 1.5 μm), a plurality of bond pads (e.g., having a height of from about 200 nm to 1.5 μm), a plurality of connectors (e.g., buried connectors, where each connector has a height of from about 50 nm to 900 nm), and a dielectric material disposed around the electrodes and bond pads (e.g., having a height of from about 500 nm to about 2 µm). In one embodiment, the connector is disposed between a dielectric layer and a bonding layer.

OTHER EMBODIMENTS

All publications, patents, and patent application mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of fabricating an electrode array, the method comprising:
    (i) providing a plurality of electrodes and a plurality of bond pads disposed on a top surface of a handle wafer, wherein the handle wafer further comprises a dielectric layer configured to isolate the plurality of electrodes and the plurality of bond pads;
    (ii) depositing a first metal to form a connector, wherein the connector is configured to form an electrical connection between at least one of the plurality of electrodes and at least one of the plurality of bond pads;
    (iii) depositing a bonding layer on at least a portion of a top surface of the dielectric layer;
    (iv) adhering a device wafer to a top surface of the bonding layer; and
    (v) removing the handle wafer, thereby forming a planar device,
    wherein the planar device comprises the device wafer, the bonding layer disposed on a surface of the device wafer, and an electrode array disposed within the dielectric layer, and
    wherein the electrode array comprises the at least one of the plurality of electrodes, the at least one of the plurality of bond pads, and the connector configured to form the electrical connection between the at least one of the plurality of electrodes and the at least one of the plurality of bond pads.

2. The method of claim 1, wherein step (ii) comprises forming the electrical connection between one electrode and one bond pad.

3. The method of claim 2, wherein step (ii) comprises forming a plurality of electrical connections, wherein each connection is between one electrode and one bond pad.

4. The method of claim 1, further comprising, after step (iii):
    planarizing the bonding layer, thereby forming a planarized bonding layer to provide the top surface of the bonding layer for step (iv).

5. The method of claim 1, further comprising an initial bonding layer disposed between the plurality of electrodes and the top surface of the handle wafer.

6. The method of claim 5, further comprising a seed layer disposed between the initial bonding layer and the plurality of electrodes.

7. The method of claim 5, further comprising, after step (iv):
    removing the initial bonding layer.

8. The method of claim 6, further comprising, after step (iv):
    removing the seed layer.

9. The method of claim 1, wherein the dielectric layer extends above a top surface of the plurality of electrodes, thereby providing a plurality of buried electrodes.

10. The method of claim 9, wherein the dielectric layer extends of from about 100 nm to about 900 nm above the top surface of the plurality of buried electrodes.

11. The method of claim 1, wherein the dielectric layer extends above a top surface of the plurality of bond pads, thereby providing a plurality of buried bond pads.

12. A method of fabricating an electrode array, the method comprising:
    (i) providing a plurality of electrodes, a plurality of bond pads, and a dielectric layer configured to isolate the plurality of electrodes and the plurality of bond pads, wherein the plurality of electrodes and the plurality of bond pads are disposed on a top surface of a stack, and wherein the stack comprises a handle wafer having a top surface, a first bonding layer disposed on the top surface of the handle wafer, and a seed layer disposed on a top surface of the first bonding layer, in which the seed layer is disposed beneath a bottom surface of the plurality of electrodes and the plurality of bond pads;
    (ii) removing a portion of the dielectric layer, thereby forming a removed pattern connecting at least one of the plurality of electrodes to at least one of the plurality of bond pads;
    (iii) depositing a first metal within the removed patterns, thereby forming an array of connectors, wherein each connector is configured to form an electrical connection between at least one of the plurality of electrodes and at least one of the plurality of bond pads;
    (iv) depositing a second bonding layer on at least a portion of a top surface of the dielectric layer;
    (v) planarizing the second bonding layer, thereby forming a planarized bonding layer;
    (vi) adhering a device wafer to a top surface of the planarized bonding layer;
    (vii) removing the handle wafer; and
    (viii) removing the first bonding layer and seed layer, thereby forming a planar device,
    wherein the planar device comprises the device wafer, the planarized bonding layer disposed on a surface of the device wafer, and an electrode array disposed within the dielectric layer, and
    wherein the electrode array comprises the plurality of electrodes, the plurality of bond pads, and the array of connectors configured to form electrical connections between at least one of the plurality of electrodes and at least one of the plurality of bond pads.

13. The method of claim 12, wherein step (iii) comprises forming the electrical connection between one electrode and one bond pad.

14. The method of claim 13, wherein step (iii) comprises forming a plurality of electrical connections, wherein each connection is between one electrode and one bond pad.

* * * * *